US008815952B1

(12) United States Patent
Carnell et al.

(10) Patent No.: US 8,815,952 B1
(45) Date of Patent: Aug. 26, 2014

(54) CHLORHEXADINE ANTISEPTIC

(71) Applicant: Carnell & Herzog, LLC, Spokane, WA (US)

(72) Inventors: Victor Carnell, Spokane, WA (US); Chris Herzog, Spokane, WA (US)

(73) Assignee: Carnell & Herzog, LLC, Spokane, WA (US)

( * ) Notice: Subject to any disclaimer, the term of this patent is extended or adjusted under 35 U.S.C. 154(b) by 0 days.

(21) Appl. No.: 13/843,391

(22) Filed: Mar. 15, 2013

(51) Int. Cl.
*A01N 37/52* (2006.01)
*A61K 31/155* (2006.01)
*A61K 31/4425* (2006.01)
*A61K 31/198* (2006.01)

(52) U.S. Cl.
CPC ........... *A61K 31/155* (2013.01); *A61K 31/4425* (2013.01); *A61K 31/198* (2013.01)
USPC ...................................................... 514/635

(58) Field of Classification Search
None
See application file for complete search history.

(56) References Cited

U.S. PATENT DOCUMENTS

| | | | |
|---|---|---|---|
| 2003/0181341 A1 | 9/2003 | Yoshimi | |
| 2004/0224897 A1 | 11/2004 | Leung et al. | |
| 2005/0260266 A1 | 11/2005 | Gebreselassie et al. | |
| 2006/0078509 A1 | 4/2006 | Gebreselassie et al. | |
| 2008/0184510 A1* | 8/2008 | Conceicao | 15/106 |
| 2009/0068122 A1* | 3/2009 | Pilch et al. | 424/52 |
| 2009/0186943 A1* | 7/2009 | Ikeda et al. | 514/635 |
| 2009/0214628 A1* | 8/2009 | de Rijk | 424/450 |
| 2010/0197621 A1 | 8/2010 | Henry et al. | |

FOREIGN PATENT DOCUMENTS

WO    WO0230469 A2    4/2002

OTHER PUBLICATIONS

Batra et al., "Efficacy and Limitation of a Chlorhexidine-based Decolonization Strategy in Preventing Transmission of Methicillin-resistant Staphylococcus aureus in an Intensive Care Unit", Clin Infect Dis. Jan. 15, 2010; 50(2), p. 210-217.
Seymour S. Block, "Disinfection, Sterilization and Preservation", Book, Lippincott Williams & Wilkins, 2001, p. 548.
Itzhak Brook, "Secondary Bacterial Infections Complicating Skin Lesions", J. Med. Microbiol, vol. 51, May 2002, 808-812.
Haley, et al., "Bactericidal Activity of Antiseptics Against Methicillin-Resistant *Staphylococcus aureus*", Journal of Clinical Microbiology, Jun. 1985, p. 991-992.
H. Roger Hart, "Improving Medicated Products with Sarcosinate Surfactants", Reprinted from Cosmetics & Toiletries, Dec. 1980, vol. 95, No. 12, p. 51-53.
J. Roger Hart, "N-acyl Sarcosine Surfactants", Reprinted from May 1979 Cosmetics & Toiletries, vol. 94, No. 5, 3 pages.
J. Roger Hart, "Sarcosinate Surfactants in Skin Cleansers", Reprinted from Cosmetic Technology, Jan. 1980, 4 pages.

(Continued)

*Primary Examiner* — Melenie McCormick
*Assistant Examiner* — Andrew Lee
(74) *Attorney, Agent, or Firm* — Lee & Hayes, PLLC; Benjamin A. Keim

(57) ABSTRACT

A composition comprising a mixture of chlorohexidine, a surfactant, and a cationic quaternary ammonium compound is suitable for use as an antiseptic and is surprisingly effective against difficult-to-kill organisms such as *Mycobacterium tuberculosis* and against Methicillin-resistant *Staphylococcus aureus* (MRSA) while still being suitable for topical application. The composition may include a chelating agent.

11 Claims, 5 Drawing Sheets

(56) References Cited

OTHER PUBLICATIONS

Ho, et al., "High rate of qacA- and qacB-positive Methicillin-resistant *Staphylococcus aureus* isolates from Chlorhexidine-impregnated Catheter-related Bloodstream Infections.", Antimicrob Agents Chemother. Nov. 2012; vol. 56, No. 11, p. 5693-5697.

McDonnell, et al., "Antiseptics and Disinfectants: Activity, Action, and Resistance", Clinical Microbiology Reviews, Jan. 1999, p. 147-179.

Peterson et al, "Comparative Evaluation of Surgical Scrub Preparations", Surg Gynecol Obstet., Jan. 1978, 146(1), pp. 63-65.

"Physiological Properties of Hamposyl Sarcosinates", Hampshire Hamposyl Surfactants, Product Brochure dated May 2000, 3 pages.

Rikimaru, et al., "Efficacy of Common Antiseptics against Mycobacteria", Int Journal Tuberc Lung Disease, 4(6), Jan. 26, 2000, 7 pages.

Russell, "Activity of Biocides against Mycobacteria", Journal of Applied Bacteriology, vol. 81, Dec. 1996 p. 87S-101S.

Shamsudin et al, "High Prevalence of qacA-B Carriage Among Clinical Isolates of Meticillin-Resistant *Staphylococcus aureus* in Malaysia", Journal of Hosptial Infection, Jul. 2012, 81(3), pp. 206-208.

Sheng et al, "Epidemiology and Susceptibilities of Methicillin-Resistant *Staphylococcus aureus* in Taiwan: Emphasis on Chlorhexidine Susceptibility", Diagnostic Microbiology andInfectious Diseases , Mar. 2009, 63(3), pp. 309-313.

"The Use of N-Acyl Sarcosinate Surfactants in Personal Care Products", Hamposyl Surfactants, Hampshire Chemical Corporation, May 2000, 35 pages.

The PCT Search Report and Written Opinion mailed Jun. 10, 2014 for PCT application No. PCT/US14/24470, 11 pages.

Seymour S. Block, "Disinfection, Sterilization and Preservation", Book, Lippincott Williams & Wilkins, 2001 (via Express Mail).

\* cited by examiner

CHLORHEXADINE ANTISEPTIC

TECHNICAL FIELD

This application relates to chlorhexidine antiseptics.

BACKGROUND

Chemicals and techniques for effectively killing pathogenic microorganisms are useful in the fields of human and veterinary medicine. Application of high heat and pressure in an autoclave is one technique to inactivate many pathogenic microorganisms. Various chemicals such as bleach, hydrogen peroxide, peracetic acid, and glutaraldehyde may be used to kill pathogenic microorganism. The difficulty of inactivating microorganisms varies with the organism. Disinfection is generally defined as including any process, chemical or physical, that destroys most pathogens but may not kill bacterial spores. Sterilization refers to methods and chemicals that destroy all viable forms of microbial life including bacterial spores. Both disinfection and sterilization generally refer to the destruction of microorganisms on non-living objects.

The difficult of inactivating microorganism can be ranked according to a scale of susceptibility. Generally, a chemical or process that kills microorganisms in a given susceptibility group will also kill microorganisms in easier-to-kill susceptibility groups. Table 1 below shows a scale of susceptibility with the more-difficult-to-kill microorganisms listed lower on the scale. Thus, if a disinfectant kills microorganisms in susceptibility group D such as *M. tuberculosis* that disinfectant will also kill microorganisms in susceptibility groups A-C.

TABLE I

Scale of Susceptibility

| Microbial Susceptibility Group | Microorganism (dried on carriers) |
| --- | --- |
| A | Retroviruses (AIDS), ortho and paramyxoviruses, herpes viruses, vaccinia, corona, and other enveloped viruses, gram negative rods and some filamentous fungi, some gram positive cocci, human hepatitis B virus |
| B | *Staphylococcus aureus*, some diphasic and filamentous fungi, yeasts and algae, some gram negative rods |
| C | Adenovirus |
| D | *Mycobacterium tuberculosis* (BCG strain), rotaviruses, reoviruses, some mold ascospores |
| E | Picornaviruses (polio, rhino), parvoviruses, hepatitis A |
| F | Bacterial endospore (*Bacillus, Clostridinium*), viroids |
| G | Prions (chronic infectious neuropathic agents, slow viruses) |

Human skin is frequently colonized with a flora that varies depending on the location on the body and the setting. Normal human skin flora may include several types of bacteria such as gram-positive cocci, gram-positive-rods, and gram-negative bacteria. Most of these types of bacterial, other than gram-positive rods such as *Bacillus* and *Clostridinium*, are categorized in microbial susceptibility groups A and B above. Thus, any solution which kills microorganisms in groups B, or any of the more-difficult-to-kill groups, would be effective against most bacterial that normally colonizes human skin.

Skin and soft tissue infections are among the most common type of infections afflicting humans. Skin and soft tissue infections may lead to serious local and systemic complications. One of the common causes of skin and soft tissue infections is the occurrence of secondary bacterial infection that complicates treatment of skin lesions. Skin lesions that can also be secondarily infected with bacteria and fungi. Thus, a skin or soft tissue infection may actually be a result of the interaction of multiple microorganisms. Examples of this type of skin lesion include, but are not limited to, skin lesions caused by scabies, psoriasis, poison ivy, atopic dermatitis, eczema herpeticum, or kerion. Oral or systemic antibiotics may be effective at treating bacteria. However, there is a delay while a systemic antibiotic moves through a patient's body to the site of infection. Additionally, antibiotics are not effective for treating infections caused by microorganisms other than bacteria. Thus, there is a need for treatment techniques that can address infections caused by multiple microorganisms.

Many of the techniques and chemicals used for disinfection and sterilization are not suitable for application to living tissue or skin. The features of such techniques which make them effective at killing pathogenic microorganisms also cause harm or death to healthy living tissue. Antimicrobial substances that are suitable for application on the skin or tissue of humans and animals are referred to as antiseptics. However, because of the design for use on living tissue, many antiseptics are less effective at killing pathogenic microorganisms than disinfectants or sterilants. Thus, there is a need for antiseptics with improved efficacy.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

An embodiment of the invention concerns a composition including chlorohexidine, a surfactant, and a cationic quaternary ammonium compound. One embodiment of the invention concerns the composition described above wherein the surfactant comprises N-acyl sarcosinate. Another embodiment of the invention concerns the composition described above wherein the cationic quaternary ammonium compound comprises cetylperidium chloride (CPC). Yet another embodiment concerns chlorohexidine, a surfactant, a cationic quaternary ammonium compound, and a chelating agent. Still another embodiment concerns the chelating agent including ethylenediaminetetraacetic acid (EDTA).

The compositions described in the disclosure are suitable for use as antiseptics due to low toxicity yet strong enough to kill or inactivate pathogenic microorganisms.

DETAILED DESCRIPTION

Figure 1:
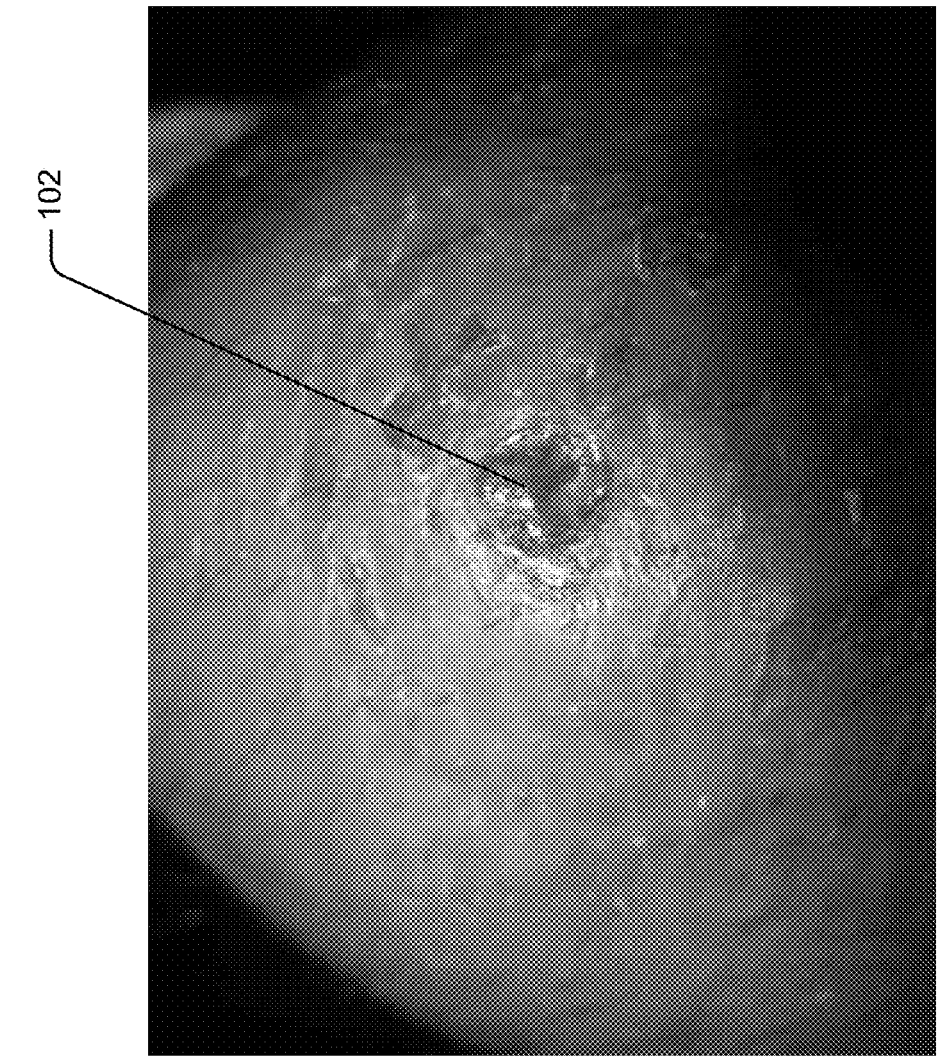
FIGS. 1-5 shows photographs of a lesion infected with MRSA healing in response to treatment with a chlorohexidine solution.

The present invention concerns compositions that are effective for killing microorganisms including, for example, difficult-to-kill microorganisms such as *Mycobacterium tuberculosis* and methicillin-resistant Staphylococcus aureus while also being suitable for topical application as an antiseptic. Disinfectants or sterilants for hard surface or "cleaning" applications may be designed to be effective against such difficult-to-kill microorganisms without regard for harm or irritation that could be caused to living tissue. Antiseptics are often less effective for killing or inactivating microorganisms because antiseptics are generally designed to cause little or no irritation to healthy, living tissue. The compositions disclosed herein are suitable for use as antiseptics, yet due to the particular combination of components show surprisingly high efficacy against even difficult-to-kill microorganisms.

Unless otherwise indicated, all numbers expressing percentages of ingredients are to be understood as indicating approximate weight/volume percentages. Accordingly, unless explicitly indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. Further, the ranges stated in this disclosure and the claims are intended to include the entire range including the endpoint(s).

According to an embodiment, the present invention concerns a composition that includes a mixture of chlorhexidine, a surfactant, and a cationic quaternary ammonium compound to form an antiseptic mixture that is more effective at inactivating pathogenic microorganisms than any of those chemicals alone. According to certain embodiments, chlorhexidine may be combined with gluconic acid to form chlorhexidine gluconate. Chlorhexidine, either as chlorhexidine gluconate, chlorhexidine hydrochloride, chlorhexidine dihydrochloride, chlorhexidine diacetate, or in another form, may be present at levels of about 0.4 to about 5 weight/volume %, or about from about 0.8 to about 1 weight/volume %, or even about 0.96 weight/volume %.

In another embodiment, the surfactant may be a nonionic surfactant or an ionic surfactant. Examples of nonionic surfactants include anhydrosorbitol esters and ethyloxated derivatives thereof. Examples of ionic surfactants include carboxylate surfactants, sulfate surfactants, and sarcosinate surfactants. According to certain embodiments, the surfactant may be present at levels of from about 0.01 to about 1 weight/volume %, from about 0.03 to about 0.1 weight/volume %, or even at about 0.05 weight/volume %. Some surfactants, for example sarcosinate surfactants, generally exhibit only minimal penetration into the stratum corneum membrane thereby maintaining membrane integrity. Sarcosinate surfactants may include, but are not limited to, sarcosine (N-methylglycine), sodium lauroyl sarcosinate, ammonium lauroyl sarcosinate, sodium cocoyl sarcosinate, sodium myristoyl sarcosinate, sodium oleoyl sarcosinate, or N-acyl sarcosinate (sarkosyl).

In an embodiment, the cationic quaternary ammonium compound may be, but is not limited to, benzalkonium chloride, benzethonium chloride, methylbenzethonium chloride, cetalkonium chloride, cetylpyridinium chloride (CPC), cetylpyridinium bromide, cetrimonium, cetrimide, dofanium chloride, tetraethylammonium bromide, or domiphen bromide. According to certain embodiments, the cationic quaternary ammonium compound may be present at levels of from about 0.01 to about 1 weight/volume %, from about 0.03 to about 0.1 weight/volume %, or even about 0.05 weight/volume %. According to certain embodiments, cationic quaternary ammonium compounds, such as CPC, are non-corrosive, effective over a wide pH range (pH 3 to 10.5), stable at high temperatures, relatively stable in the presence of organic matter, and exhibit low irritation and low toxicity.

According to one embodiment, the present invention concerns a composition that comprises a mixture of chlorhexidine, a surfactant, a cationic quaternary ammonium compound as presented above together with a chelating agent. The chelating agent may be, but is not limited to, ethylenediaminetetraacetic acid (EDTA); diethylenetriaminepentaacetic acid (DPTA); Aminotrimethylene phosphonic acid, Beta-Alanine Diacetic Acid, Calcium Disodium ethylenediaminetetraacetic acid (EDTA), Citric Acid, Cyclodextrin, Cyclohexanediamine Tetraacetic Acid, Diammonium Citrate, Diammonium EDTA, Diethylenetriamine Pentamethylene Phosphonic Acid, Dipotassium EDTA, Disodium Azacycloheptane Diphosphonate, Disodium EDTA, Disodium Pyrophosphate, EDTA, Etidronic Acid (HEDP, Hydroxyethylidene diphosphonic acid), Galactaric Acid, Gluconic Acid, Glucuronic Acid, HEDTA, Hydroxypropyl Cyclodextrin, Methyl Cyclodextrin, Pentapotassium Triphosphate, Methyl glycine diacetic acid (MGDA), Pentasodium Aminotrimethylene Phosphonate, Pentasodium Ethylenediamine Tetramethylene Phosphonate, Pentasodium Pentetate, Pentasodium Triphosphate, Pentetic Acid, Phytic Acid, Polyamine, Potassium Citrate, Potassium EDTMP, Potassium Gluconate, Potassium Polyphosphate, Potassium Trisphosphonomethylamine Oxide, Ribonic Acid, Sodium Chitosan Methylene Phosphonate, Sodium Citrate, Sodium Diethylenetriamine Pentamethylene Phosphonate, Sodium Dihydroxyethylglycinate, Sodium EDTMP, Sodium Gluceptate, Sodium Gluconate, Sodium Glycereth-1 Polyphosphate, Sodium Hexametaphosphate, Sodium Metaphosphate, Sodium Metasilicate, Sodium Phytate, Sodium Polydimethylglycinophenolsulfonate, Sodium Trimetaphosphate, TEA-EDTA, TEA-Polyphosphate, Tetrahydroxyethyl Ethylenediamine, Tetrahydroxypropyl Ethylenediamine, Tetrapotassium Etidronate, Tetrapotassium Pyrophosphate, Tetrasodium EDTA, Tetrasodium Etidronate, Tetrasodium Pyrophosphate, Tripotassium EDTA, Trisodium Dicarboxymethyl Alaninate, Trisodium EDTA, Trisodium HEDTA, Trisodium MGDA, Trisodium N, N-bis(carboxymethyl)glycine (NTA), or Trisodium Phosphate. The chelating agent may be included at levels of from about 0.05 to about 2 weight/volume %, or from about 0.08 to about 1 weight/volume %, or even about 0.1 weight/volume %.

A liquid solution containing 0.96% chlorhexidine gluconate, 0.05% N-acyl sarcosinate, 0.1% CPC, and 0.1% EDTA may be used to kill or inactivate enveloped viruses, non-enveloped viruses, gram-positive bacteria, gram-negative bacteria, fungi, and other microorganisms. This liquid solution is also tuburculocidal; it can kill *Mycobacterium tuberculosis*. This level of efficacy corresponds to microbial susceptibility group A-D shown in Table 1. Surprisingly, the efficacy against mycobacteria, such as *M. tuberculosis*, is much greater than any of the components separately at the listed concentrations. The liquid solution may be made with an aqueous solvent such as water or a saline solution with a salinity and acidity appropriate for the intended application.

Many disinfectants or sterilants are effective at killing microorganisms on hard surfaces, but are too harsh for application to living tissue (e.g., bleach). However, the chlorhexidine solutions disclosed herein provide the additional surprising benefit of being non-irritating and suitable for application on sensitive tissue. Chlorhexidine gluconate is used, for example, in a 4% weight/volume solution as a surgical hand scrub without harm to skin. The concentrations of chlorohexidine discussed herein generally are at the same or lower levels then the level used for surgical hand scrubs. Sarcosinate surfactants exhibit only minimal penetration into the skin thereby reducing the potential for harm or irritation to skin or other tissue. Additionally, CPC exhibits low irritation and low toxicity.

Embodiments of the present invention may be formulated as, for example, aqueous mixtures, gels, creams, lotions, emulsions, or dry powders. Antiseptics based on any embodiment of the present invention may be used for applications including, but not limited to, pre-surgical skin scrubs, field antiseptics for trauma/military situations, veterinary treatment of mange or similar skin diseases, or an irrigant when performing root canal therapy. Due to the high level of efficacy in killing microorganisms this antiseptic mixture may, unlike other antiseptics, be used in applications where sexually transmitted diseases (STDs), MRSA (methicillin-resistant Staphylococcus aureus), and/or mycobacteria such as *Mycobacterium tuberculosis* are present.

The following examples are submitted for a better understanding of the invention.

EXAMPLES

Example 1

In this example, the test composition comprises 0.96% chlorhexidine gluconate, 0.05% N-acyl sarcosinate, 0.1% EDTA, and 0.1% CPC. This example tests for tuberculocidal properties of the test solution. The microorganism used in the test was *Mycobacterium bovis*. *M. bovis* causes tuberculosis in cattle and is related to *M. tuberculosis* which causes tuberculosis in humans. Efficacy against *M. bovis* indicates efficacy against *M. tuberculosis*. Referring to the scale of susceptibility shown in Table 1, the efficacy against *M. tuberculosis*, which is in microbial susceptibility group D, also indicates efficacy against microorganisms in the easier-to-kill groups A-C.

A 0.1 mL aliquot of *M. bovis* culture inoculum was added to 10 mL of the test composition identified above. The test composition had a pH of about 5.5. Efficacy was tested after five minutes of exposure and after 10 minutes of exposure. A total of five replicates were used for each time period. A neutralizer was added to stop the activity of the test composition at the end of the time periods. None of the five replicates tested positive for presence of *M. bovis* after either five minutes or 10 minutes of exposure. Test results are provided below in Table 2.

TABLE II

Number of positive tests out of 5 replicates

| Organism | 5 minutes | 10 minutes |
|---|---|---|
| *Mycobacterium bovis* | 0 | 0 |

The results of example 1 show efficacy of the test composition, which is suitable for topical use as an antiseptic, against *M. tuberculosis*.

Example 2

In this example, five different test compositions were prepared. Test composition 1 was 0.96% chlorhexidine gluconate, 0.05% N-acyl sarcosinate, 0.1% EDTA, and 0.1% CPC. Test composition 2 was 0.05% N-acyl sarcosinate, 0.1% EDTA, and 0.1% CPC. Test composition 3 was 0.96% chlorhexidine gluconate, 0.1% EDTA, and 0.1% CPC. Test composition 5 was 0.96% chlorhexidine gluconate, 0.05% N-acyl sarcosinate, and 0.1% CPC.

The microorganism used in the test was *Mycobacterium smegmatis*. *M. smegmatis* is a non-pathogenic bacteria related to *M. tuberculosis* which causes tuberculosis in humans. Efficacy against *M. smegmatis* indicates efficacy against *M. tuberculosis*.

Example 2 includes in-vitro time-kill tests performed for each of the five test composition listed in the preceding paragraph against *M. smegmatis*. *M. smegmatis* suspension with an inoculum level of $9.150 \times 10^6$ colony-forming unit (CFU)/ML was used for all tests. A 0.1 mL aliquot of the *M. smegmatis* suspension was added to 9.9 mL of the respective test compositions and exposed for periods of one minute, five minutes, and 10 minutes. At the end of each exposure period, a neutralizer was added to stop bactericidal activity of the test compositions.

Test composition 1 was effective in reducing the number of CFU/mL at each exposure length and achieved a greater than 2.5 $Log_{10}$ reduction after 10 minutes of exposure. Test results are provided below in Table 3.

TABLE III

Post-exposure population change (test composition 1)

| Organism | Exposure Time (minutes) | Post-exposure population (CFU/ML) | $Log_{10}$ reduction | Percent reduction |
|---|---|---|---|---|
| *Mycobacterium smegmatis* | 1 | $1.8050 \times 10^6$ | 0.7049 | 80.2732 |
| | 5 | $5.40 \times 10^4$ | 2.2290 | 99.4098 |
| | 10 | $1.020 \times 10^4$ | 2.9528 | 99.8885 |

This shows that test composition 1 is effective against *M. tuberculosis*. This supports the results of example 1.

Test composition 2, without chlorhexidine gluconate, did not kill *M. smegmatis* after one or five minutes of exposure. Test results are provided below in Table 4. The test substance was not fully inactivated during the test with 10 minutes of exposure. Thus, the detected efficacy may be higher than it would have been if the bactericidal properties of the test substance were fully inactivated when the neutralizer was added. True efficacy is likely lower than the efficacy shown in Table 4.

TABLE IV

Post-exposure population change (test composition 2)

| Organism | Exposure Time (minutes) | Post-exposure population (CFU/ML) | $Log_{10}$ reduction | Percent reduction |
|---|---|---|---|---|
| *Mycobacterium smegmatis* | 1 | $1.0750 \times 10^7$ | 0.0000 | 0.0000 |
| | 5 | $1.0950 \times 10^7$ | 0.0000 | 0.0000 |
| | *10 | $7.1 \times 10^6$ | 0.1101 | 22.4044 |

*Test substance not fully inactivated by neutralizer

This shows that a composition without chlorhexidine has reduced antiseptic properties.

Test composition 3, without a surfactant (e.g., N-acyl sarcosinate) had similar efficacy to that of test composition 1. However, test composition 3 was not fully inactivated for any of the tests. Thus, efficacy results would likely be lower if there was full neutralization. Test results are provided below in Table 5.

TABLE V

Post-exposure population change (test composition 3)

| Organism | Exposure Time (minutes) | Post-exposure population (CFU/ML) | $Log_{10}$ reduction | Percent reduction |
|---|---|---|---|---|
| *Mycobacterium smegmatis* | *1 | $1.950 \times 10^6$ | 0.6714 | 78.6885 |
| | *5 | $3.850 \times 10^4$ | 2.3759 | 99.5792 |
| | *10 | $6.950 \times 10^3$ | 3.1194 | 99.9240 |

*Test substance not fully inactivated by neutralizer

Although this test appears to show minimal effect on efficacy when a surfactant is omitted from the composition, results when there is effective neutralization would likely show a larger decrease in antiseptic properties. Thus, this suggests that addition of a surfactant increases efficacy.

Test composition 4, without a cationic quaternary ammonium compound (e.g., CPC) showed decreased efficacy against *M. smegmatis*. However, test composition 4 was not fully inactivated at any of the time points. Thus, efficacy results would likely be even lower if there was full neutralization. Test results are provided below in Table 6.

TABLE VI

Post-exposure population change (test composition 4)

| Organism | Exposure Time (minutes) | Post-exposure population (CFU/ML) | $Log_{10}$ reduction | Percent reduction |
|---|---|---|---|---|
| Mycobacterium smegmatis | *1 | $4.350 \times 10^6$ | 0.3229 | 52.4590 |
| | *5 | $6.250 \times 10^5$ | 1.1655 | 93.1694 |
| | *10 | $2950 \times 10^5$ | 1.4616 | 96.7760 |

*Test substance not fully inactivated by neutralizer

This shows that inclusion of a cationic quaternary ammonium compound increases efficacy.

Test composition 5, without a chelating agent (e.g., EDTA), showed decreased efficacy against *M. smegmatis* but still achieved a greater than 2.5 $Log_{10}$ reduction after 10 minutes of exposure. Test results are provided below in Table 7.

TABLE VII

Post-exposure population change (test composition 5)

| Organism | Exposure Time (minutes) | Post-exposure population (CFU/ML) | $Log_{10}$ reduction | Percent reduction |
|---|---|---|---|---|
| Mycobacterium smegmatis | 1 | $2.3550 \times 10^6$ | 0.5894 | 74.2623 |
| | 5 | $1.2150 \times 10^5$ | 1.8768 | 98.6721 |
| | 10 | $2.3250 \times 10^4$ | 2.5950 | 99.7459 |

This shows that a chelating agent may be omitted without significant decreases in the ability to kill or inactivate microorganisms in at least some situations.

The tests in example 2, taken together, show that each of the separate compounds included in test composition 1, with the possible exception of the chelating agent, contributes the efficacy as an antiseptic against bacteria that cause tuberculosis. This combinatorial effect was both surprising and unexpected.

Example 3

In this example, the test composition comprises 0.96% chlorhexidine gluconate, 0.05% N-acyl sarcosinate, 0.1% EDTA, and 0.1% CPC. This example compares the test composition to a solution of 4% chlorhexidine gluconate. The microorganism used in the test was methicillin-resistant *Staphylococcus aureus*. Methicillin-resistant *Staphylococcus aureus* (MRSA) is a strain of *S. aureus* that is resistant to beta-lactam antibiotics.

An in-vitro time-kill test was performed on *S. aureus* using both the test composition and the solution of 4% chlorhexidine gluconate. A *S. aureus* suspension with an inoculum level of $1.460 \times 10^7$ colony-forming units (CFU)/ML was used for all tests. A 0.1 mL aliquot of the *S. aureus* suspension was added to 9.9 mL of the test composition or the 4% chlorhexidine gluconate solution and exposed for periods of one minute, five minutes, and 10 minutes. At the end of each exposure period, a neutralizer was added to stop the bactericidal activity. Test results are provided below in Tables 8 and 9.

TABLE VIII

Post-exposure population change (test composition)

| Organism | Exposure Time (minutes) | Post-exposure population (CFU/ML) | $Log_{10}$ reduction | Percent reduction |
|---|---|---|---|---|
| Staphylococcus aureus | 1 | $2.350 \times 10^1$ | 4.7933 | 99.9984 |
| | 5 | $<1.00 \times 10^1$ | 6.1644 | 99.9999 |
| | 10 | $<1.00 \times 10^1$ | 6.1644 | 99.9999 |

TABLE IX

Post-exposure population change (4% chlorhexidine gluconate)

| Organism | Exposure Time (minutes) | Post-exposure population (CFU/ML) | $Log_{10}$ reduction | Percent reduction |
|---|---|---|---|---|
| Staphylococcus aureus | 1 | $1.2150 \times 10^3$ | 4.0798 | 99.9917 |
| | 5 | $<1.00 \times 10^1$ | 6.1644 | 99.9999 |
| | 10 | $<1.00 \times 10^1$ | 6.1644 | 99.9999 |

The results of example 3 show that the test composition achieves results similar to 4% chlorhexidine gluconate solution with only one-quarter as much chlorhexidine gluconate. Chlorhexidine may be irritating to sensitive tissue at high concentrations, so achieving similar efficacy with a lower concentration is a benefit.

Example 4

This example shows the efficacy of a chlorhexidine solution including 0.48% chlorhexidine gluconate, 0.05% N-acyl sarcosinate, 0.1% EDTA, and 0.1% CPC for treating a lesion infected with MRSA. Example 4 also shows a lack of irritation to the surrounding tissue over a month-long course of application. The treatment process included (1) spraying or apply the chlorhexidine solution on the infected site and leaving wet for one minute, (2) after one minute placing a gauze pad thoroughly saturated with the chlorhexidine solution over the lesion and affixing in place with tape, (3) repeating steps (1) and (2) at least twice daily to remove the purulent matter exuding from the lesion; (4) covering the lesion at night to maintain sterility, and (5) repeating steps (1)-(4) until the exudate from lesion ceases.

Figure 2:
Figure 3:
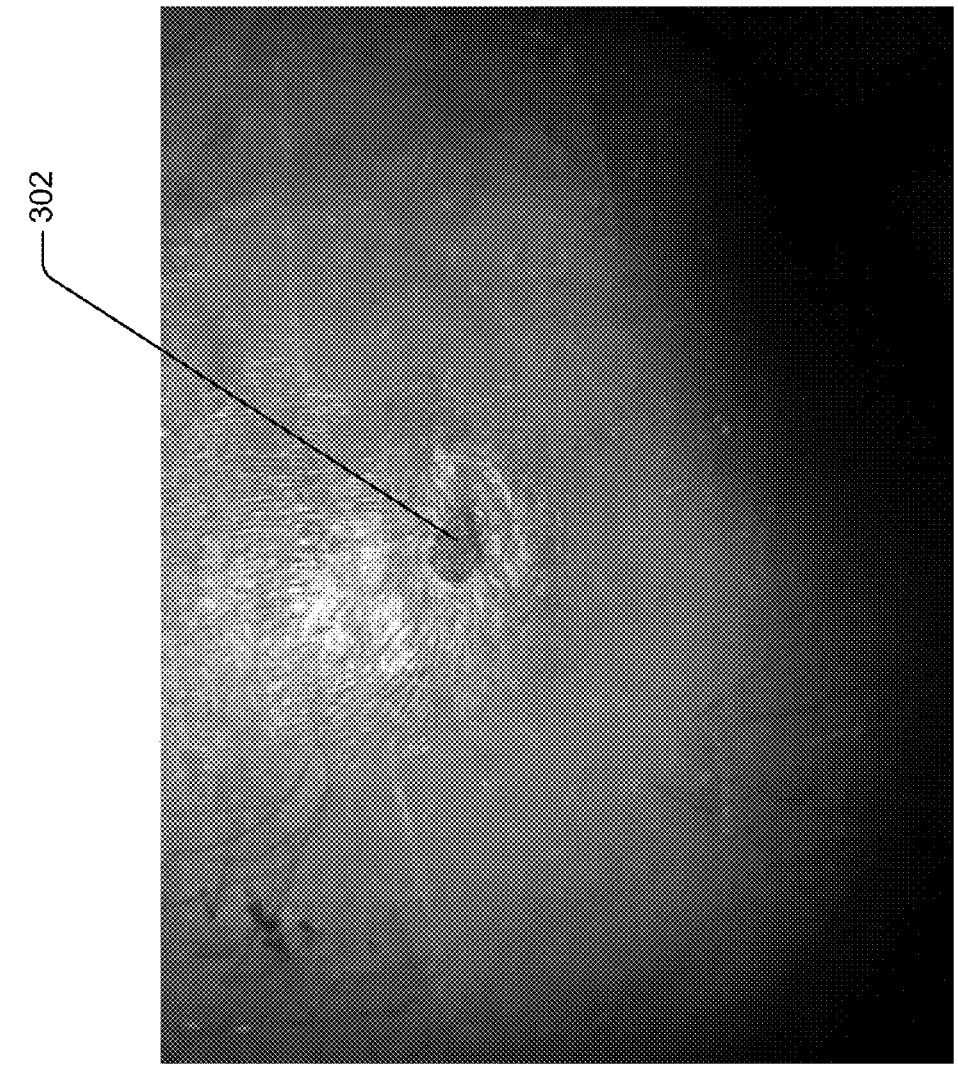
Figure 4:
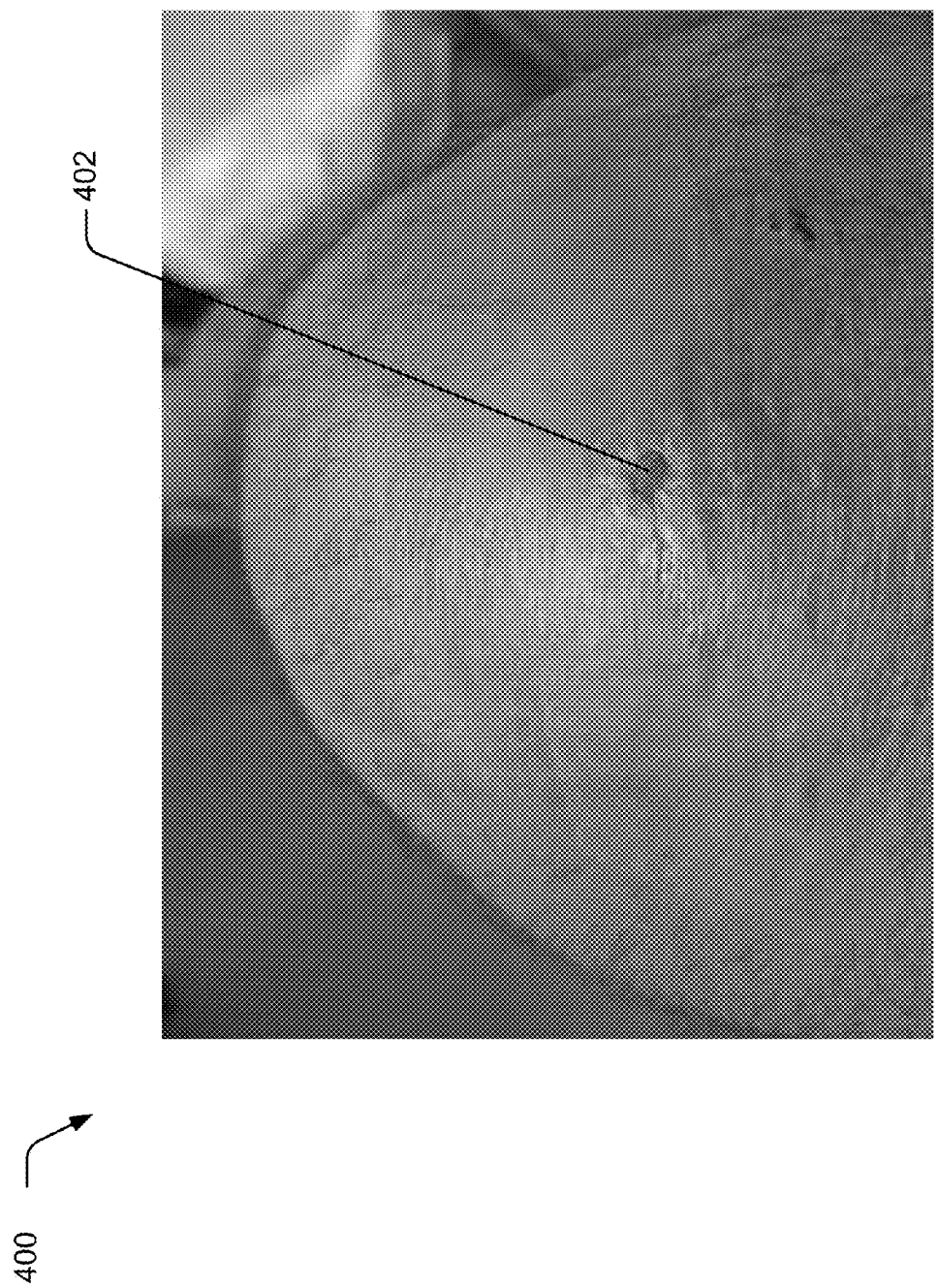
Figure 5:
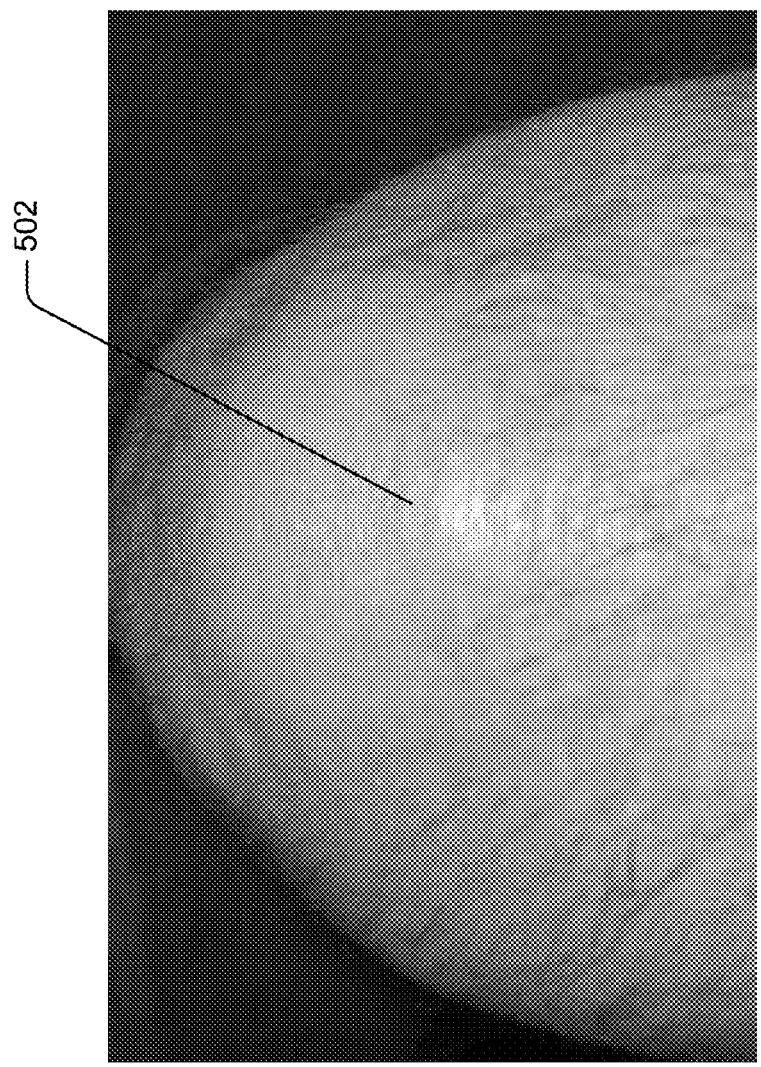

FIGS. 1-5 show the healing of a MRSA infected lesion on a human knee in response to application of the chlorhexidine solution. FIG. 1 shows a picture 100 of the knee with the lesion 102 prior to treatment. The patient reported a feeling of immediate relief upon application of the chlorhexidine solution and did not report any irritation or discomfort due to the chlorhexidine solution. FIG. 2 shows a picture 200 of the knee and a slightly smaller lesion 202 after 5-8 days of treatment. FIG. 3 shows a picture 300 of the knee with the lesion 303 exhibiting significantly less purulent matter following an additional 5-8 days of treatment. FIG. 4 shows a picture 400 of the knee with the lesion 402 reduced in size following additional 5-8 days of treatment. FIG. 5 shows a photograph 500 of the knee following healing of the lesion 502. The photograph 500 in FIG. 5 was taken 5-8 days after the photograph 400 of FIG. 4. The total time from the start of treatment until the condition shown in the final photograph 500 was about one month. Moreover, after approximately 60 applications (i.e., twice daily for a month) including prolonged contact with saturated gauze pads, the epidermis of the knee shows no signs of irritation.

Although the subject matter of this disclosure has been described in language specific to chemical composition and/or methodological steps, it is to be understood that the invention defined in the appended claims is not necessarily limited to the chemical compositions or methods described above. Rather, the specific chemical compositions and methods are disclosed as illustrative techniques for implementing the claims.

The invention claimed is:

1. A composition comprising:
   chlorhexidine or a salt thereof present at about 0.96 weight/volume %;
   N-acyl sarcosinate present at about 0.05 weight/volume %;
   cetylpyridinium chloride (CPC), cetylpyridinium bromide, or mixtures thereof present at about 0.1 weight/volume %; and
   ethylenediaminetetraacetic acid (EDTA) present at about 0.1 weight/volume %.

2. The composition of claim 1, wherein the chlorhexidine comprises a gluconate salt.

3. A composition comprising:
   chlorhexidine or a salt thereof present at about 0.96 weight/volume %;
   a sarcosinate surfactant present at about 0.05 weight/volume %;
   cetylpyridinium chloride (CPC), cetylpyridinium bromide, or mixtures thereof present at about 0.1 weight/volume %; and
   ethylenediaminetetraacetic acid (EDTA) present at about 0.1 weight/volume %.

4. A method of killing or inactivating *Mycobacterium* spp., *Staphylococcus aureus*, or both present on tissue of a patient, the method comprising:
   contacting the tissue of the patient with a composition according to claim 1.

5. The composition of claim 3, wherein the sarcosinate surfactant comprises N-acyl sarcosinate.

6. A method of killing or inactivating microorganisms present on tissue of a patient, the method comprising:
   contacting the tissue of the patient with a composition according to claim 1, wherein the microorganisms are selected from the group consisting of: *Mycobacterium tuberculosis* (BCG strain), rotaviruses, reoviruses, mold ascopores, picornaviruses (polio, rhino), parvoviruses, hepatitis A, bacterial endospores (*Bacillus, Clostridinium*), viroids, and prions (chronic infectious neuropathic agents, slow viruses).

7. A method of killing or inactivating microorganisms present on tissue of a patient, the method comprising:
   contacting the tissue of the patient with a composition according to claim 3, wherein the microorganisms are selected from the group consisting of: *Mycobacterium tuberculosis* (BCG strain), rotaviruses, reoviruses, mold ascopores, picornaviruses (polio, rhino), parvoviruses, hepatitis A, bacterial endospores (*Bacillus, Clostridinium*), viroids, and prions (chronic infectious neuropathic agents, slow viruses).

8. The composition of claim 1 further comprising a solvent.

9. The method of claim 4, wherein the *Mycobacterium* spp. comprises *M. tuberculosis, M. bovis, M. smegmatis*, or mixtures thereof.

10. The composition of claim 8, wherein the solvent comprises water or a saline solution.

11. The method of claim 4, wherein the *S. aureus* comprises methicillin-resistant *S. aureus* (MRSA).

* * * * *